United States Patent [19]

Colsher

[11] Patent Number: 4,610,258

[45] Date of Patent: Sep. 9, 1986

[54] METHOD FOR CALCULATING BLOOD FLOW USING FREELY DIFFUSIBLE INERT GASES AND CT

[75] Inventor: James G. Colsher, Waukesha, Wis.

[73] Assignee: General Electric Company, Milwaukee, Wis.

[21] Appl. No.: 670,594

[22] Filed: Nov. 13, 1984

[51] Int. Cl.[4] .............................................. A61B 5/02
[52] U.S. Cl. ................................................... 128/691
[58] Field of Search ............... 128/653, 659, 691, 716, 128/719

[56] References Cited

PUBLICATIONS

Haughton, V. et al, "Clinical Cerebral BF Measurement with Inhaled Xenon and CT", AJR 134: 281–283, 1978.
Kelz, F. et al, "Computed Tomographic Measurement of the Xenon Brain–Blood Partition Coefficient and Implications for Regional Cerebral BF", Radiology 127: 385–392 1978.
Gur, D. et al, "Progress in Cerebrovascular Disease: Local Cerebral BF by Xenon Enhanced CT," Stroke 13: 750–758, 1982.
Forsythe, G. E. et al, "Computer Methods for Mathematical Computations," Prentice Hall, Inc. (no date available).
Gur, D. et al, "Xenon and Iodine Enhanced Cerebral CT: A Closer Look," Strohe 12: 573–578, 1981.
De Fontaine, D. L. et al, "A Fast Non–Linear Least Squares Method for the Calculation of Relaxation Times," Jrnl. of Mag. Resonance, 18: 276–281 (1975).
Haughton, V. M. et al, "A Clinical Evaluation of Xenon Enhancement for Computed Tomography", Investigative Radiology, Supp. to vol. 15, No. 6, 5160–5163.
Palla, R. S. et al, "Regional Cerebral BF Measurements Using Stable Xenon Enhanced CT: A Theoretical and Exp. Evalution," Jrnl. of Comp. Asstd. Tomog. 8(4): 619–630, Aug. 1984.
Wagner, P. D. et al, "Measurement of Continuous Distributions of Ventilation–Perfusion Ratios: Theory", Jrnl. Appl. Physiology, vol. 36, No. 5, May 1974, pp. 588–599.
Fuller, G. et al, "Analytic Geometry and Calculus," Ch. 18: Partial Differentiation Section 18-13 Maxima and Minima, pp. 518–522.

*Primary Examiner*—Kyle L. Howell
*Assistant Examiner*—Francis J. Jaworski
*Attorney, Agent, or Firm*—Flehr, Hohbach, Test, Albritton & Herbert

[57] ABSTRACT

A simplified method of determining tissue blood flow such as cerebral blood flow is provided by calculating the partial derivatives with respect to flow rate constant (k) and partition coefficient ($\lambda$) of the sum of errors squared for calculated tissue concentration of a diffusible inert gas such as xenon minus measured tissue concentration of xenon based on CT numbers.

13 Claims, No Drawings

METHOD FOR CALCULATING BLOOD FLOW USING FREELY DIFFUSIBLE INERT GASES AND CT

This invention relates generally to blood flow measurements, and more particularly the invention relates to such blood flow measurements using freely diffusible inert gases such as xenon as a contrasting agent and computed tomography (CT) for detecting the gases.

CT reconstructed images of the brain can provide an indication of blood flow in cerebral tissue. The use of inhaled xenon and CT for clinical blood flow measurements is known. See, for example, Haughton et al, "Clincal Cerebral Blood Flow Measurement With Inhaled Xenon and CT", AJR 134:281–283, 1978 and Kelcz et al "Computed Tomographic Measurement of the Xenon Brain-Blood Partition Coefficient and Implications for Regional Cerebral Blood Flow: A Preliminary Report", Radiology 127:385–392, 1978.

Briefly, a mixture of air and xenon (e.g. 30% xenon) is breathed by a patient and measurements of expired gas are assumed to be proportional to xenon concentrations in arterial blood. Flow of the xenon enriched blood in the brain is then detected by CT measurements of brain tissue since xenon is an attenuator of x-rays, thus producing increased CT numbers.

In general, the tissue concentration of xenon as a function of time is assumed to be given by:

$$C(t) = \lambda k \int_0^t C_a(u) e^{-k(t-u)} du \quad (1)$$

where
- $\lambda$ is the partition coefficient
- $k$ is the rate constant
- $f = \lambda k$ is flow/volume
- $C_a(t)$ is the arterial concentration of xenon as a function of time (See Kety S. S., "The Theory and Applications of the Exchange of Inert Gas at the Lungs and Tissues", Pharmacol, Rev. 3:1–41, 1951).

In the preferred technique $C_a(t)$ can be determined by measuring the xenon concentration at end tidal expiration, as noted above, since it has been shown that it is proportional to xenon concentration in arterial blood.

The values for $C(t)$ are obtained by taking CT scans while the patient is breathing the mixture of xenon and air (enhanced scans) and CT scans while the patient is breathing a non-xenon containing gas (baseline scans). The measured values of xenon based on CT numbers are compared with calculated values of xenon, and differences therein are used to identify values of the rate constant and the partition coefficient. From a mathematical point of view, the solution of the equation is a non-linear least squares problem. More particularly, values of $k$ and $\lambda$ are found that minimize $$F = \sum_t W_t \left[ \lambda k \int_0^t C_a(u) e^{-k(t-u)} du - C(t) \right]^2 \quad (2)$$

where F is the sum of the errors squared and $W_t$ are weights. The sum is over the series of discrete samples (C(t)).

Previous attempts to solve this problem have used generalized non-linear least squares algorithms, such as disclosed by Ip, W., "Local Cerebral Hemodynamics by Tracing Stable Xenon with Transmission Computed Tomography", Ph.D. Thesis University of Wisconsin Madison, 1981; and Gur, D., et al, "Progress in Cerebrovascular Disease: Local Cerebral Blood Flow by Xenon Enhanced CT:, Stroke 13:750–758, 1982.

However, the non-linear least squares routine is complicated and thus slow to calculate.

Accordingly, an object of the present invention is an improved method of calculating local blood flow in tissue.

Another object of the invention is an improved method of determining blood flow based on CT measurements of blood flow and calculated measurements of blood flow.

A feature of the invention is calculating the partial derivatives of the sum of the errors squared, based on the difference of CT measurements and calculated measurements, with respect to the partition coefficient, $\lambda$, and the rate constant, $k$, assuming that the partial derivatives are zero when the sum of errors squared is a minimum.

Referring to equation (2) above, the partial derivatives with respect to partition coefficient, $\lambda$, and rate coefficient, $k$, are given as follows:

$$0 = \frac{\partial F}{\partial \lambda} = 2 \sum_t W_t \left\{ \lambda k \int_0^t C_a(u) e^{-k(t-u)} du - C(t) \right\} \quad (3)$$

$$k \int_0^t C_a(u) e^{-k(t-u)} du$$

$$0 = \frac{\partial F}{\partial k} = 2 \sum_t W_t \left\{ \lambda k \int_0^t C_a(u) e^{-k(t-u)} du - C(t) \right\}$$

$$\lambda \int_0^t C_a(u)(1 - kt + ku) e^{-k(t-u)} du$$

These two equations can be rearranged to give $$\lambda = \frac{\sum_t W_t C(t) G(t,k)}{\sum_t W_t E(t,k) G(t,k)} = \frac{\sum_t W_t C(t) E(t,k)}{\sum_t W_t E^2(t,k)} \quad (4)$$

ps where $$E(t,k) = k \int_0^t C_a(u) e^{-k(t-u)} du \quad (5)$$

$$G(t,k) = \int_0^t C_a(u)(1 - kt + ku) e^{-k(t-u)} du$$

The value of $k$ can now be determined using well known techniques to find the zero of a function of one variable. See Gill et al., *Practical Optimization*, Academic Press, New York, 1981.

In any practical implementation a functional form for $C_a(t)$ is generally assumed. For example, it may be assumed that $C_a(t)$ can be described by $$C_a(t) = A(1 - e^{-mt}) \quad (6)$$

where

A is a maximum concentration
M is the rate constant.
Equations (5) can then be integrated to give $$E(t,k) = A\left(1 + \frac{me^{-kt} - ke^{-mt}}{k - m}\right) \quad (7)$$

$$G(t,k) = \frac{A}{m - k}\left(mte^{-kt} + me^{-mt} + \frac{me^{-kt} - ke^{-mt}}{k - m}\right)$$

This assumption implies that all the data (CT scans) were acquired during the washin of xenon. Since the method is independent of the functional form of $C_a(t)$ one could assume a biexponential such as $$C_a(t) = A(1 - ae^{-mt} - be^{-nt}) \quad (8)$$

Functional forms for washout and washin-washout can also be handled by this technique.

The model (see equation 1) for tissue concentration can be extended to include a background term (see Ip. W. "Local Cerebral Hemodynamics by Tracing Stable Xenon With Transmission Computed Tomography", Ph.D. Thesis University of Wisconsin Madison 1981) as follows:

$$c(t) = \lambda \int_0^t C_a(u)e^{-k(t-u)}du + b \quad (9)$$

The method of taking partial derivatives can be shown to apply to this model also.

$$\lambda = \frac{N\Sigma W_i C(t)E(t,k) - \Sigma W_i C(t)\Sigma W_i E(t,k)}{N\Sigma W_i E^2(t,k) - (\Sigma W_i E(t,k))^2} \quad (10)$$

$$= \frac{N\Sigma W_i C(t)G(t,k) - \Sigma W_i C(t)\Sigma W_i G(t,k)}{N\Sigma W_i E(t,k)G(t,k) - \Sigma W_i E(t,k)\Sigma W_i G(t,k)}$$

where $$E(t,k) = k \int_0^t C_a(u)e^{-k(t-u)}du$$

$$G(t,k) = \int_0^t C_a(u)(1 - kt + ku)e^{-k(t-u)}du$$

The solution of partial derivatives was proposed by D. E. Fontaine et al to find values of spin lattice relaxation times in nuclear magnetic resonant calculations. See D. Fontaine et al, "A Fast Non-Linear Least Squares Method for the Calculation of Relaxation Times", J. Magnetic Resonance 18:276–281, 1975. While the problem of finding relaxation times is different, from blood flow measurements, the approach taken by D. Fontaine et al is mathematically similar in using partial derivatives.

The invention has been implemented using a Data General S 140 Computer in a General Electric 9800 CT Scanner. Attached hereto and incorporated by reference is a printout of the computer programs implementing the invention as run in the Data General Computer. This implementation was faster by a factor of three over the prior art method of finding partition coefficient and rate constant from solution of the equation for the sum of the square of errors.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

```

#          "DESC - Xenon Cbf

     subroutine DixCfls(Ier)

#purpose: create the flow & mean sq error files from the (up to 6)
#         smoothed enhancement images.

#author:  G.E. Medical Systems
#         Computer  Engineering
#         Peter S. Schiltz

#arguments:
     integer Ier                    #return status

#subroutines called:
#            Dierrs  - display error reporting
#            DixPre  - precompute some often-used values
#            DixCflB - compute all the flow & lambda values
#            DiPick  - get char from keyboard
#            DiOvl   - load DixCflB
#            DixMep  - mean squared error processing

#include files used:
%         INCLUDE 'DIDATA.IR'    ; display common
%         INCLUDE 'DIXNOD1.IR'   ; global commons for nodel buffers
%         INCLUDE 'DIXNOD2.IR'   ; global commons for node2 buffers
%         INCLUDE 'DIXXPF.IR'    ; parameter values for xenon cbf
%         INCLUDE 'PICKCOM.IR'   ; common area for DiPick
%         INCLUDE 'DEXCODES.IR'  ; character definitions
%         INCLUDE 'F5ERR.FR'     ; parameter values for FORTRAN error codes
```

```

#library routines called: Close - close a unit
#                          Dfil  - delete any previous file of this name
#                          Cfil  - create a file
#                          Open  - open a file
#                          SetBf - set buffer to IGNORE
#                          WrBlk - flush output buffers

#notes:   DixCflB consists of the central loop of this calculation.
#         We call it using DiOvl.
#         Output at a given position in the image is as follows:
If there are less than MINENH valid pixels at the position,
#                     new value will be -32768 (= IGNORE). This will be the
#                     case wherever all the input images have been masked.
#              If DixZof can't succeed, the new value will be -32768.
#              Otherwise the new value will be whatever is returned by DixZof.
#         Assumes MAXENH, the max. no. of enhanced images, is <= 9.

#         "REV 0        PSS              15-Sep-83
#         "REV 1        KGC              13-DEC-83
#                                        SECOND CLINICAL VERSION

#*****************************************************************

#         "ETX
define(OK,1)              #'no error' return code
define(READONLY,1)        #mode for input files
define(RANDOM,2)          #file type to create
define(EXCLUSIVE, 3)      #open mode for output file
define(BLOCKSIZE,256)     #no. pixels per block overlay DivxCfls
    compiler static;  implicit integer (a-z)

external DivxCflB, DixCflB integer AbCode, Stat    #error handling
    real Pixel              #loop counter: the pixel under consideration
    real Rtime(MAXENH)      #Rtime(i) = time of i-th enhancement image in minute
    real Mt(MAXENH)         #Mt(i) = MVal * Rtime(i)
    real Expmmt(MAXENH)     #Expmmt(i) = exp(-Mt(i))
    integer ipts(MAXENH)    #the corresponding pixels found in the (up to MAXENH
                            #input files. Some of these values may be invalid
                            #(=IGNORE) and must be removed before calling DixZof
    integer nValid          #number of valid pixels
    real EnhVal(MAXENH)     #the valid pixels
    real TmeVal(MAXENH)
     #the values from 'tme' which correspond to valid pixels
    real MtVal(MAXENH)      #the values from 'mt' which correspond to valid pixels
    real ExpVal(MAXENH)     #the values from 'exp' which correspond to valid pixel:
    real Rate, Lambda       #flow rate & partition coefft. returned from dixzof
    integer TotalBlocks     #total no. blocks in input files
    integer InP, OutP       #positions in input & output buffers, respectively, of
                            #next available pixel or pixel slot.
    integer NextBlockIn, ReadSize   #next read from input files: block to start
                            #at, no. blocks to read
    integer NextBlockOut, WriteSize #next write to output files: block to start
                            #at, no. blocks to write
    integer FileName(3)     #building input filenames: 'SMTHn', n=1..6
    integer i, k            #loop indices
    integer Result          #result code from DiPick call
    equivalence(Result,i)

#These equivalence statements put all our variables into the 'Extra' buffer
#Had to do this when I ran out of space in the node; also allows sharing of
#these variables between this routine and DixCflB.
    equivalence (Rate, Extra(1))
    equivalence (Lambda, Extra(3))
    equivalence (Pixel, Extra(5))
    equivalence (AbCode, Extra(7))
    equivalence (Stat, Extra(8))
```

```
      equivalence (i, Extra(9))
      equivalence (k, Extra(10))
      equivalence (nValid, Extra(11))
      equivalence (InP, Extra(12))
      equivalence (OutP, Extra(13))
      equivalence (NextBlockIn, Extra(14))
      equivalence (NextBlockOut, Extra(15))
      equivalence (ReadSize, Extra(16))
      equivalence (WriteSize, Extra(17))
      equivalence (TotalBlocks, Extra(18))
      equivalence (FileName(1), Extra(19))
      equivalence (Mt(1), Extra(22))
      equivalence (Expmmt(1), Extra(2*MAXENH + 22))
      equivalence (EnhVal(1), Extra(4*MAXENH + 22))
      equivalence (TmeVal(1), Extra(6*MAXENH + 22))
      equivalence (MtVal(1), Extra(8*MAXENH + 22))
      equivalence (ExpVal(1), Extra(10*MAXENH + 22))
      equivalence (Rtime(1), Extra(12*MAXENH + 22))
      equivalence (ipts(1), Extra(14*MAXENH + 22))

#-------------------------------------------------------------
#ask user if we should proceed
#   proceed if he types 'Y'; return if he types 'N';  else ask again
#-------------------------------------------------------------

AbCode = 5                              #;[Pick error]
   repeat {
      write(ANLU,200)
      200 format(/3x,"Calculations starting - Continue? (Y/N): ", z)
      Call DiPick (DPGETASC, 1, Result)
      goto (201, 202, 202, 7000, 202, 202, 7000) Result
      goto 7000

201   if (DpFstChr == DEXY)  break
            if (DpFstChr == DEXN)  {
               Ier = 0;  return
               }

202   write(ANLU,205);  205 format(/5x,"Invalid Command.")

}

#-------------------------------------------------------------
#compact 'Etime' array into 'Rtime' array
------------------------------------------------------------- k = 0
   for (i = 1;  i <= MAXENH & k < nEnh;  i = i + 1)
      if (Etime(i) != IGNORE) {
         k = k + 1;  Rtime(k) = float(Etime(i))/60.
         }

#-------------------------------------------------------------
#initialize
#-------------------------------------------------------------

NextBlockIn = 0;  NextBlockOut = 0
   TotalBlocks = ifix((TotalWords + BLOCKSIZE. - 1.)/BLOCKSIZE.) #round up
   ReadSize = PRESZ/BLOCKSIZE;  WriteSize = POSTSZ/BLOCKSIZE
   InP = PRESZ + 1;  OutP = 1
   call DixPre(Mval, nEnh, Rtime, Mt, Expmmt)

#-------------------------------------------------------------
#open input files
------------------------------------------------------------- do i = 1, nEnh {
```

```
      AbCode = 10                    #;[close error]
      call Close(FreLuArr(i), Ier);  if (Ier != OK & Ier != ERFOP) goto 7000
      AbCode = 20                    #;[encode error]
      encode(FileName, 100, err=7000) i;  100 format('SMTH', i1, '<NUL>')
      AbCode = 30                    #;[input file open error]
      call Open(FreLuArr(i), FileName, READONLY, Ier)
      if (Ier != OK)  goto 7000
      }
```

```
#------------------------------------------------------------
#open output files: FLOWF
#------------------------------------------------------------

AbCode = 40               #;[close error]
   call Close(Imglu, Ier);   if (Ier != OK & Ier != ERFOP)  goto 7000

AbCode = 50               #;[file delete error]
   call Dfil('FLOWF', Ier);  if (Ier != OK & Ier != ERDLE)  goto 7000

AbCode = 60               #;[output file create error]
   call Cfil('FLOWF', RANDOM, Ier);  if (Ier != OK)  goto 7000

AbCode = 70               #;[output file open error]
   call Open(Imglu, 'FLOWF', EXCLUSIVE, Ier)
   if (Ier != OK)  goto 7000

#------------------------------------------------------------
#... and ERRXE
#------------------------------------------------------------

AbCode = 80               #;[close error]
   call Close(Sctlu, Ier);   if (Ier != OK & Ier != ERFOP)  goto 7000

AbCode = 90               #;[file delete error]
   call Dfil('ERRXE', Ier);  if (Ier != OK & Ier != ERDLE)  goto 7000

AbCode = 100              #;[output file create error]
   call Cfil('ERRXE', RANDOM, Ier);  if (Ier != OK)  goto 7000

AbCode = 110              #;[output file open error]
   call Open(Sctlu, 'ERRXE', EXCLUSIVE, Ier)
   if (Ier != OK)  goto 7000

#------------------------------------------------------------
#overlay DixCflB on top of myself, to do the main loop through the pixels
#------------------------------------------------------------

ErrWrd = OK
   Call DiOvl (DIVXCFLB, DIXCFLB, DIVXCFLS, $120)
   120 if (ErrWrd != OK)   {
      Ier = ErrWrd;  goto 7100
      }

#------------------------------------------------------------
#all done; write output buffers if necessary, close files, delete input files
#close & delete input files
------------------------------------------------------------ do i = 1, nEnh {
      AbCode = 130               #;[input file close error]
      call Close(FreLuArr(i), Ier);  if (Ier != OK)  goto 7000
      AbCode = 140               #;[encode error]
      encode(FileName, 100, err=7000) i    #format is in 'open input files' lo(
      AbCode = 150               #;[input file delete error]
      call Dfil(FileName, Ier);  if (Ier != OK)  goto 7000
      }
```

```
#-----------------------------------------------------------
#write output buffers if necessary
----------------------------------------------------------- if (OutP > 1) {                     #have to write buffers
        call SetBf(Flow(OutP), POSTSZ- OutP*2 + 1, IGNORE)   #fill them with
        call SetBf(Msqe(OutP), POSTSZ - OutP*2 + 1, IGNORE)  #invalid pixels
        WriteSize = (OutP + BLOCKSIZE - 1)/BLOCKSIZE
        AbCode = 160                    #;[write block error]
        call WrBlk(ImgLu, NextBlockOut, Flow, WriteSize, Ier)
        if (Ier != OK)   goto 7000
        AbCode = 170                    #;[write block error]
        call WrBlk(SctLu, NextBlockOut, Msqe, WriteSize, Ier)
        if (Ier != OK)   goto 7000
        }

#-----------------------------------------------------------
#close output files
#-----------------------------------------------------------

AbCode = 180         #;[output file close error]
    call Close(ImgLu, Ier);   if (Ier != OK)   goto 7000
    AbCode = 190         #;[output file close error]
    call Close(SctLu, Ier);   if (Ier != OK)   goto 7000

#-----------------------------------------------------------
#call DixMpe to do the main loop through the pixels
#-----------------------------------------------------------

ErrWrd = OK
    Call DixMep
    if (ErrWrd != OK)    {
        Ier = ErrWrd;  goto 7100
        }

#-----------------------------------------------------------
#errors & returns
----------------------------------------------------------- go to 9000          #normal return 7000    call Dierrs("DixCfls",AbCode,Ier)
7100    do i = 1, nEnh
            call Close(FreLuArr(i), Stat)
        call Close(ImgLu, Stat)
        call Close(SctLu, Stat)

9000    return end

SUBROUTINE DIXPRE ( M        , NUMVAL , TMEVAL , MT       , EXPMMT )
C
C==============================================================================
C
C       "DESC            D E S C R I P T I O N
C
C------------------------------------------------------------------------------
C
C       DOES SOME PRELIMINARY CALCULATIONS THAT ARE USED IN LATER FITTING
C       ROUTINES - DIXFCN AND DIXMSE
C
```

```
C===============================================================================
C
C                         I N P U T S
C
C-------------------------------------------------------------------------------
C
        REAL            M                       ; ARTERIAL RATE CONSTANT
     $                  TMEVAL (MAXVAL)         ; TIMES
C
        INTEGER         NUMVAL                  ; NUMBER OF VALUES
C
C===============================================================================
C
C                         O U T P U T S
C
C-------------------------------------------------------------------------------
C
        REAL            MT     (MAXVAL) ,       ; M * TMEVAL
     $                  EXPMMT (MAXVAL)         ; EXP ( -MT )
C
C===============================================================================
C
C                         R E V I S I O N S
C
C-------------------------------------------------------------------------------
C
C       "REV 0          7/08/83                 J. G. COLSHER
C
C       "REV 1          7/18/83                 J. G. COLSHER
C         ADDED CALCULATION OF MT AND DEFINED CALLING SEQUENCE
C
C       "ETX
C
C===============================================================================
C
C                         C A L U L A T I O N S
C
C-------------------------------------------------------------------------------
C
        DO 300 NVAL = 1,NUMVAL
C
            MT(NVAL)     = M * TMEVAL(NVAL)
            EXPMMT(NVAL) = EXP ( - MT(NVAL) )
C
  300   CONTINUE
C
        INCLUDE "DIXPRM.IR"
C
        RETURN

#       "DESC - Xenon Cbf

   subroutine DixCflB

#purpose: create the flow & mean sq error files from the (up to 6)
#         smoothed enhancement images.

#author:  G.E. Medical Systems
#         Computer  Engineering
#         Peter S. Schiltz

#subroutines called:
#               Dierrs - display error reporting
#               DixZof - compute flow(p) & lambda(p) from enh(i,p), i=1..6

#include files used:
%       INCLUDE 'DIDATA.IR'     ; display common
%       INCLUDE 'DIXNOD1.IR'    ; global commons for node1 buffers
%       INCLUDE 'DIXNOD2.IR'    ; global commons for node2 buffers
%       INCLUDE 'DIXXPF.IR'     ; parameter values for xenon cbf
%       INCLUDE 'PICKCOM.IR'    ; COMMON FOR DIPICK
%       INCLUDE 'F5ERR.FR'      ; parameter values for FORTRAN error codes
```

```

#library routines called: RdBlk - read from enhancement image files
#                         WrBlk - write to flow/partition coefft. files
#                         SetBf - set buffer to IGNORE

#notes:  This routine performs the main loop of the DixCfls calculation.
#        It is called via an overlay load (DiOvl) from DixCfls.
#        Output at a given position in the image is as follows:
If there are less than MINENH valid pixels at the position,
#                       new value will be 100000K (= IGNORE). This will be the
#                       case wherever all the input images have been masked.
#               If DixZof can't succeed, the new value will be 100000K.
#               Otherwise the new value will be whatever is returned by DixZof.

#       "REV 0          PSS                     15-Sep-83
#       "REV 1          KGC                     13-DEC-83
#                       SECOND CLINICAL VERSION

#***************************************************************

#       "ETX
define(OK,1)            #'no error' return code
define(BLOCKSIZE,256)   #no. pixels per block
define(FAILED,100000K)          #DixZof couldn't fit a curve to the Enh values
define(LAMMIN,35.)              #minimum value allowed for 100*Lambda
define(RIGNORE,100000K)         #real ignore value overlay DivxCflB
    compiler static; implicit integer (a-z)

integer AbCode, Stat    #error handling
    real Pixel              #loop counter: the pixel under consideration
    real Rtime(MAXENH)      #Rtime(i) = time of i-th enhancement image in minutes
    real Mt(MAXENH)         #Mt(i) = MVal * Rtime(i)
    real Expmmt(MAXENH)     #Expmmt(i) = exp(-Mt(i))
    integer ipts(MAXENH)    #the corresponding pixels found in the (up to MAXENH)
                            #input files. Some of these values may be invalid
                            #(=IGNORE) and must be removed before calling DixZof
    integer nValid          #number of valid pixels
    real EnhVal(MAXENH)     #the valid pixels
    real TmeVal(MAXENH)
      #the values from 'tme' which correspond to valid pixels
    real MtVal(MAXENH)      #the values from 'mt' which correspond to valid pixels
    real ExpVal(MAXENH)     #the values from 'exp' which correspond to valid pixels
    real Rate, Lambda       #flow rate & partition coefft. returned from dixzof
    real TotMSE,TotMSQ      #total mean squared error, total mean sq. error squared
    REAL MSE                #MEAN SQUARED ERROR
    real MseCtr             #counter or valid entries
#   real MsEAve, MsQAve     #mean squared error averages
#   real Std                #standard deviation
#   real MSQT               #mean sqared root
    double precision MsEAve,MsQAve,Std,Msqt integer TotalBlocks     #total no. blocks in input files
    integer InP, OutP       #positions in input & output buffers, respectively, of
                            #next available pixel or pixel slot.
    integer NextBlockIn, ReadSize  #next read from input files: block to start
                                   #at, no. blocks to read
    integer NextBlockOut, WriteSize#next write to output files: block to start
                                   #at, no. blocks to write
    integer FileName(3)     #building input filenames: 'SMTHn', n=1..6
    integer i, k            #loop indices

#These equivalence statements put all our variables into the 'Extra' buffer
#Had to do this when I ran out of space in the node
    equivalence (Rate, Extra(1))
    equivalence (Lambda, Extra(3))
    equivalence (Pixel, Extra(5))
    equivalence (AbCode, Extra(7))
    equivalence (Stat, Extra(8))
```

```
        equivalence (i, Extra(9))
        equivalence (k, Extra(10))
        equivalence (nValid, Extra(11))
        equivalence (InP, Extra(12))
        equivalence (OutP, Extra(13))
        equivalence (NextBlockIn, Extra(14))
        equivalence (NextBlockOut, Extra(15))
        equivalence (ReadSize, Extra(16))
        equivalence (WriteSize, Extra(17))
        equivalence (TotalBlocks, Extra(18))
        equivalence (FileName(1), Extra(19))
        equivalence (Mt(1), Extra(22))
        equivalence (Expmmt(1), Extra(2*MAXENH + 22))
        equivalence (EnhVal(1), Extra(4*MAXENH + 22))
        equivalence (TmeVal(1), Extra(6*MAXENH + 22))
        equivalence (MtVal(1), Extra(8*MAXENH + 22))
        equivalence (ExpVal(1), Extra(10*MAXENH + 22))
        equivalence (Rtime(1), Extra(12*MAXENH + 22))
        equivalence (ipts(1), Extra(14*MAXENH + 22))

TotMSE = 0.; TotMSQ = 0.; MseCtr = 0.

#-------------------------------------------------------------
#main loop: for each pixel in the output files, do:
------------------------------------------------------------- write(ANLU,1008);  1008 format(/)
   for (Pixel = 1.;  Pixel <= TotalWords;  Pixel = Pixel + 1.) {

#-------------------------------------------------------------
#   get next set of input pixels in 'ipts', reading buffer if empty
------------------------------------------------------------- if (InP > PRESZ) {           #need to read buffers
            if (NextBlockIn + ReadSize > TotalBlocks)    #last read?
                ReadSize = TotalBlocks - NextBlockIn
            if (mod(NextBlockIn, 20) == 0) {
                write(ANLU,1009) NextBlockIn, TotalBlocks
                1009 format(/5x,"READING BLOCK ",i4," OF ", i4)
                }
            do i = 1, min(nEnh, 4) {      #read Dixnod2 buffers
                AbCode = 120             #;[rdblock error]
                call RdBlk(FreLuArr(i), NextBlockIn, Ei(1, i), ReadSize, ErrWrd)
                if (ErrWrd != OK)  goto 7000
                }
            for (i = 5;  i <= nEnh;  i = i + 1) {    #read Dixnod1 buffers
                AbCode = 130             #;[rdblock error]
                call RdBlk(FreLuArr(i), NextBlockIn, Eii(1, i - 4), ReadSize,
                        ErrWrd)
                if (ErrWrd != OK)  goto 7000
                }
            InP = 1;  NextBlockIn = NextBlockIn + ReadSize
            }           #end of 'read buffers' section do i = 1, min(nEnh, 4)       #get next pixel from Dixnod2 buffers
                ipts(i) = Ei(InP, i)
        for (i = 5;  i <= nEnh;  i = i + 1)       #... and from Dixnod1 buffers
                ipts(i) = Eii(InP, i - 4)
        InP = InP + 1

#-------------------------------------------------------------
#    build arrays containing only valid input pixels
------------------------------------------------------------- nValid = 0
        do k = 1, nEnh
            if (ipts(k) != IGNORE) {
                nValid = nValid + 1;  EnhVal(nValid) = float(ipts(k))
                MtVal(nValid) = Mt(k);  ExpVal(nValid) = ExpMmt(k)
                TmeVal(nValid) = Rtime(k)
                }
```

```
#---------------------------------------------------------------
#   calculate flow Rate & Lambda (partition coefficient)
--------------------------------------------------------------- if (nValid >= MINENH)           # enough valid points
           call DixZof(nValid, TmeVal, EnhVal, AVal, MVal, MtVal, ExpVal,
                       Rate, Lambda)

#---------------------------------------------------------------
#   store Rate & Lambda in output buffers
--------------------------------------------------------------- if (OutP > POSTSZ/2) {     #have to write output buffers - they're full
           AbCode = 140                  #;[write block error]
           call WrBlk(ImgLu, NextBlockOut, Flow, WriteSize, ErrWrd)
           if (ErrWrd != OK)  goto 7000
           AbCode = 150                  #;[write block error]
           call WrBlk(SctLu, NextBlockOut, Msqe, WriteSize, ErrWrd)
           if (ErrWrd != OK)  goto 7000
           OutP = 1;  NextBlockOut = NextBlockOut + WriteSize
           }     #end of write buffer section if (nValid < MINENH) {        #not enough valid points
           Flow(OutP) = RIGNORE;  Msqe(OutP) = RIGNORE
           }
        else if (Rate == float(FAILED)) {
           Flow(OutP) = RIGNORE;  Msqe(OutP) = RIGNORE
           }
        else {
           Lambda = 100.*Lambda
           if (Lambda < LAMMIN)
              Flow(OutP) = 0.
           else [
              Flow(OutP) = Rate*Lambda + Sign(0.5,Rate*Lambda)
              if (Flow(OutP) > 400.)   Flow(OutP) = RIGNORE
              ]
           if (Flow(OutP) == RIGNORE)
              Msqe(OutP) = RIGNORE
           else [
              Call DixMse(Rate,Lambda/100,MVal,AVal,nValid,TmeVal,EnhVal,
                          MtVal,ExpVal,MSE)
              Msqe(OutP) = MSE
              TotMSE = TotMSE + MSE              #Total mean squared
              TotMSQ = TotMSQ + (MSE**2)         #Total mean sq err sq'd
              MseCtr = MseCtr + 1.
              ]
           }
        OutP = OutP + 1

#---------------------------------------------------------------
#   end main loop
#---------------------------------------------------------------
        }
#    PROMPT FOR HEMATOCRIT
#400     CONTINUE
#        ABCODE = 10                           #;[PICK ERROR]
#        WRITE(ANLU,500)
#500     FORMAT(/,3X,"ENTER THRESHOLD VALUE: ",Z)
#        CALL DIPICK(DPGETFP,80,RESULT)
#        GO TO (1000,600,600,600,600,600,600) RESULT
#        GO TO 600            #OK,NULL,BKUP,CNCL,SPCL,FAIL,ERR

# 600    WRITE(ANLU,650)
#650     FORMAT(/,5X,"INVALID COMMAND")
#        GO TO 400

#1000    THRESHOLD = DPFPVAL

#---------------------------------------------------------------
#   figure out somevalue value
#---------------------------------------------------------------
```

```
        MsEAve = TotMSE / MseCtr        #sum of error average
        MsQAve = TotMSQ / MseCtr        #sum of squares average
%X      TYPE "MsEAVE = ",MSEAVE," MsQAVE = ",MSQAVE
        MSQT = MSQAVE - (MSEAVE **2)
%X      TYPE "MSQT = ",MSQT
        Std = SQRT(MSQT)                # standard deviation
%X      TYPE "STD = ",STD," STDVAL = ",STDVAL
#       write(anlu,6000)MsEAve,MsQAve
#6000    format(/,3X,"MsEAve,MsQAve = ",D12.4,1X,D12.4)
#       write(anlu,6001)Msqt,Std
#6001    format(/,3X,"Msqt,Std = ",D12.4,1X,D12.4)
        Somevalue = MsEAve + (1.5*Std)    #somevalue value
#       Somevalue = MsEAve + (Std*STDVAL)   #somevalue value
#       SOMEVALUE = THRESHOLD
%X      TYPE "SOMEVALUE = ",SOMEVALUE

#----------------------------------------
#errors & returns
---------------------------------------- go to 9000        #normal return 7000    call Dierrs("DixCf1B",AbCode,ErrWrd)

9000    return end

SUBROUTINE DIXZOF ( NUMVAL , TMEVAL , ENHVAL , ARTENH , M
     $                      MT      , EXPMMT , RATE    , LAMBDA )
C
C================================================================================
C
C       "DESC       D E S C R I P T I O N
C
C--------------------------------------------------------------------------------
C
C       A ZERO OF THE FUNCTION IS COMPUTED USING AN ALGORITHM CALLED ZEROIN
C       DEVELOPED BY VAN WIJINGAARDEN , DEKKER AND OTHERS . THIS IS A FORTRAN
C       IMPLEMENTATION OF A IMPROVED VERSION DESCRIBED BY BRENT. SEE FORSTYHE,
C       GE, MA MALCOLM AND CB MOLER,  "COMPUTER METHODS FOR MATHEMATICAL
C       COMPUTATIONS", PRENTICE-HALL .
C
C================================================================================
C
C                   I N P U T S
C
C--------------------------------------------------------------------------------
C
        INTEGER     NUMVAL              ; NUMBER OF ENHANCED VALUES
C
        REAL        TMEVAL (MAXVAL) ,   ; TIME VALUES IN MINUTES
     $              ENHVAL (MAXVAL) ,   ; ENHANCEMENT VALUES
     $              ARTENH          ,   ; ARTERIAL ENHANCEMENT
     $              M               ,   ; ARTERIAL RATE CONSTANT
     $              MT      (MAXVAL) ,  ; M * TMEVAL
     $              EXPMMT (MAXVAL)     ; EXP ( - M * TMEVAL )
C
C================================================================================
C
C                   O U T P U T S
C
C--------------------------------------------------------------------------------
C
        REAL        RATE                ; RATE CONSTANT OF TISSUE (K)
     $              LAMBDA              ; PARTITION COEFFICIENT
C
```

```
C=================================================================
C
C                        R E V I S I O N S
C
C-----------------------------------------------------------------
C
C         "REV 0         7/27/83              J. G. COLSHER
C
C         "REV 1         8/02/83              J. G. COLSHER
C          DEFINED THE CALLING ARGUMENT LIST AND ELIMINATED COMMON
C
C         "REV 2         9/09/83              J. G. COLSHER
C          ADDED ABILITY TO CLAMP LAMBDA TO MAX VALUE AND CALCULATE
C          RATE CONSTANT FOR THIS FIXED LAMDBA.
C
C         "REV 3         10/12/83             J. G. COLSHER
C          REMOVED THE INITIAL CHECK FOR ZERO CROSSING AND REPLACED
C          IT WITH A CHECK FOR NUMBER OF FUNCTION CALLS
C
C         "ETX
C
C=================================================================
C
C                   D A T A    D E C L A R A T I O N S
C
C-----------------------------------------------------------------
C
      REAL         A        , B        , C        ,
     $             FCNATA   , FCNATB   , FCNATC   ,   ; FUNCTION AT A,B,C
     $             D        , E        ,
     $             HAVCMB   , TOLINT   , DEL      ,
     $             P        , Q        , R        ,
     $             S
C
      LOGICAL      LAMCLP                              ; LAMBDA CLAMP
C
      INTEGER      NCALLS
C
C=================================================================
C
C              S E T U P - EVALUATE FUNCTION AT LIMITS
C
C-----------------------------------------------------------------
C
      LAMCLP = .FALSE.
   50 A      = RCLWLM                                  ; LOWER LIMIT
      CALL DIXFCN ( A      , NUMVAL , TMEVAL , ENHVAL , M       ,
     $              MT     , EXPMMT , LAMCLP , LAMBDA , FCNATA )
C
      B      = RCUPLM                                  ; UPPER LIMIT
      CALL DIXFCN ( B      , NUMVAL , TMEVAL , ENHVAL , M       ,
     $              MT     , EXPMMT , LAMCLP , LAMBDA , FCNATB )
C
      NCALLS = 0
C
C=================================================================
C
C                    B E G I N N I N G   S T E P
C
C-----------------------------------------------------------------
C
  200 C      = A
      FCNATC = FCNATA
      D      = B - A
      E      = D
C
```

```
C================================================================================
C
C                   KEEP B AS CLOSEST APPROXIMATION TO ZERO
C
C--------------------------------------------------------------------------------
C
  300    IF ( ABS ( FCNATC ) .GE. ABS ( FCNATB ) ) GO TO 400
C
            A       = B                              ; SWAP A,B,C
            B       = C
            C       = A
            FCNATA  = FCNATB                         ; SWAP FCN AT A,B,C
            FCNATB  = FCNATC
            FCNATC  = FCNATA
C
C================================================================================
C
C                   C O N V E R G E N C E   T E S T
C
C--------------------------------------------------------------------------------
C
  400    TOLINT = TWOEPS * ABS ( B ) + HAVTOL
         HAVCMB = 0.5   * ( C - B )
         IF ( ABS ( HAVCMB ) .LT. TOLINT    .OR.
     $              FCNATB   .EQ. 0.0     ) GO TO 900
C
C================================================================================
C
C                   IS BISECTION NECESSARY
C
C--------------------------------------------------------------------------------
C
         IF ( ABS ( E )        .LT. TOLINT    .OR.
     $        ABS ( FCNATA ) .LE. ABS ( FCNATB ) ) GO TO 700
C
C================================================================================
C
C                   IS QUADRATIC INTERPOLATION POSSIBLE
C
C--------------------------------------------------------------------------------
C
         IF (  A  .NE.  C ) GO TO 500
C
C================================================================================
C
C                   LINEAR INTERPOLATION
C
C--------------------------------------------------------------------------------
C
         S       = FCNATB / FCNATA
         P       = 2.0 * HAVCMB * S
         Q       = 1.0 - S
         GO TO 600
C
C================================================================================
C
C                   INVERSE QUADRATIC INTERPOLATION
C
C--------------------------------------------------------------------------------
C
  500    Q       = FCNATA / FCNATC
         R       = FCNATB / FCNATC
         S       = FCNATB / FCNATA
C
         P       = S * ( 2.0 * HAVCMB * Q * ( Q - R )
     $                   - ( B - A ) * ( R - 1.0 ) )
C
         Q       = ( Q - 1.0 ) * ( R - 1.0 ) * ( S - 1.0 )
C
```

```
C==============================================================================
C
C                       A D J U S T    S I G N S
C
C------------------------------------------------------------------------------
C
  600    IF ( P .GT. 0.0 ) Q = -Q
         P        = ABS ( P )
C
C==============================================================================
C
C                    IS INTERPOLATION ACCEPTABLE
C
C------------------------------------------------------------------------------
C
         IF ( 2.0 * P .GE. 3.0 * HAVCMB * Q - ABS ( TOLINT * Q )
     $       .OR. P .GE. ABS ( 0.5 * E * Q )    ) GO TO 700
         E        = D
         D        = P / Q
         GO TO 800
C
C==============================================================================
C
C                         B I S E C T I O N
C
C------------------------------------------------------------------------------
C
  700    D        = HAVCMB
         E        = D
C
C==============================================================================
C
C                       C O M P L E T E    S T E P
C
C------------------------------------------------------------------------------
C
  800    A        = B
         FCNATA = FCNATB
         DEL      = D
         IF ( ABS ( D ) .LE. TOLINT ) DEL = SIGN ( TOLINT , HAVCMB )
         B        = B + DEL
C
         NCALLS = NCALLS + 1
         IF ( NCALLS .LT. 50 ) GO TO 850
            RATE   = RELFLG
            LAMBDA = RELFLG
            RETURN
C
  850    CALL DIXFCN ( B        , NUMVAL , TMEVAL , ENHVAL , M        ,
     $                 MT       , EXPMMT , LAMCLP , LAMBDA , FCNATB )
C
         IF ( SIGN ( 1.0 , FCNATB ) .EQ. SIGN ( 1.0 , FCNATC ) ) GO TO 200
         GO TO 300
C
C==============================================================================
C
C                              D O N E
C
C------------------------------------------------------------------------------
C
  900    CONTINUE
         RATE     = B
         LAMBDA = LAMBDA / ARTENH
C
         IF ( LAMBDA .LE. LAMMAX .OR. LAMCLP )    GO TO 950
            LAMCLP = .TRUE.
            LAMBDA = LAMMAX * ARTENH
            GO TO 50
C
  950    RETURN
C
```

```
        INCLUDE         "DIXPRM.IR"
C
        END
        SUBROUTINE DIXFCN ( RATE    , NUMVAL , TMEVAL , ENHVAL , M       ,
     $                      MT      , EXPMMT , LAMCLP , LAMBDA , FCNVAL )
C
C================================================================================
C
C       "DESC          D E S C R I P T I O N
C
C--------------------------------------------------------------------------------
C
C       EVALUATES THE FUNCTION AT THE INPUT PARAMETER VALUE FOR RATE CONSTANT.
C       THIS VERSION ASSUMES WASHIN ONLY .
C
C================================================================================
C
C                      I N P U T S
C
C--------------------------------------------------------------------------------
C
        INTEGER        NUMVAL                   ; NUMBER OF ENHANCED VALUES
C
        REAL           RATE              ,      ; RATE CONSTANT (PRESENT GUESS)
     $                 TMEVAL (MAXVAL) ,        ; TIME VALUES IN MINUTES
     $                 ENHVAL (MAXVAL) ,        ; ENHANCEMENT VALUES
     $                 M                 ,      ; ARTERIAL RATE CONSTANT
     $                 MT     (MAXVAL) ,        ; M * TMEVAL
     $                 EXPMMT (MAXVAL)          ; EXP ( - MT )
C
        LOGICAL        LAMCLP                   ; LAMBDA CLAMP
C
C================================================================================
C
C                      O U T P U T S
C
C--------------------------------------------------------------------------------
C
        REAL           LAMBDA                   ; PARTITION COEFFICIENT * ARTER
     $                 FCNVAL                   ; VALUE OF FUNCTION
C
C================================================================================
C
C                      R E V I S I O N S
C
C--------------------------------------------------------------------------------
C
C       "REV 0         7/18/83        J.G.COLSHER
C
C       "REV 1         8/03/83        J.G.COLSHER
C          DEFINED CALLING SEQUENCE AND ELIMINATED COMMON
C
C
C       "REV 2         9/09/83        J.G.COLSHER
C          ADDED ABILITY TO CLAMP LAMBDA
C
C       "ETX
C
C================================================================================
C
C                      D A T A    D E C L A R A T I O N S
C
C--------------------------------------------------------------------------------
C
        REAL    KMM,    KMMINV, KT,     MEXMKT, KEXMMT
C
```

```
C==============================================================================
C
C                       S E T U P
C
C------------------------------------------------------------------------------
C
      KMMINV  = 1.0 / ( RATE - M )
C
      SUM1    = 0.0
      SUM2    = 0.0
      SUM3    = 0.0
      SUM4    = 0.0
C
C==============================================================================
C
C                       C A L C U L A T I O N
C
C------------------------------------------------------------------------------
C
      DO 400 NVAL   = 1 , NUMVAL
C
              KT      = RATE * TMEVAL(NVAL)
              EXPMKT  = EXP ( - KT )                    ; UNDERFLOW SET TO 0.0
C
              MEXMKT  = M * EXPMKT
              KEXMMT  = RATE * EXPMMT(NVAL)
C
              TEMPA   = 1.0 + KMMINV * ( MEXMKT - KEXMMT )
              TEMPB   = 1.0 - MT(NVAL) * EXPMKT -
     $                                EXPMMT(NVAL) - TEMPA
C
              SUM1    = SUM1 + ENHVAL(NVAL) * TEMPA
              SUM2    = SUM2 + ENHVAL(NVAL) * TEMPB
              SUM3    = SUM3 + TEMPA * TEMPA
              SUM4    = SUM4 + TEMPA * TEMPB
C
  400 CONTINUE
C
  600 IF ( .NOT. LAMCLP ) LAMBDA = SUM1 / SUM3         ; FOR CLAMP DON'T CHANG
      FCNVAL = LAMBDA        - SUM2 / SUM4
C
      RETURN
C
      INCLUDE "DIXPRM.IR"
C
      END
      SUBROUTINE DIXMSE ( RATE    , LAMBDA , M       , ARTENH , NUMVAL ,
     $                    TMEVAL  , ENHVAL , MT      , EXPMMT , MSE    )
C
C==============================================================================
C
C     "DESC           D E S C R I P T I O N
C
C------------------------------------------------------------------------------
C
C     EVALUATES THE MEAN SQUARED ERROR GIVEN THE FITTED PARAMETER AND THE
C     DATA POINTS.
C
C==============================================================================
C
C                       I N P U T S
C
C------------------------------------------------------------------------------
C
      REAL            RATE           ,           ; RATE CONSTANT
     $                LAMBDA         ,           ; PARTITION COEF
     $                M              ,           ; ARTERIAL RATE CONSTAN
     $                ARTENH         ,           ; ARTERIAL ENHANCEMENT
     $                TMEVAL (MAXVAL),           ; TIMES
     $                ENHVAL (MAXVAL),           ; ENHANCEMENT VALUES
     $                MT     (MAXVAL),           ; M * TMEVAL
```

```
C      $             EXPMMT (MAXVAL)                  ; EXP ( -MT )
C
       INTEGER       NUMVAL                           ; NUMBER VALUES
C
C================================================================================
C
C                    O U T P U T S
C
C--------------------------------------------------------------------------------
C
       REAL          MSE                              ; MEAN SQUARED ERROR
C
C================================================================================
C
C                    R E V I S I O N S
C
C--------------------------------------------------------------------------------
C
C      "REV 0        7/27/83        J.G.COLSHER
C
C      "REV 1        8/04/83        J.G.COLSHER
C       DEFINED CALLING SEQUENCE
C
C      "ETX
C
C================================================================================
C
C                    D A T A   D E C L A R A T I O N S
C
C--------------------------------------------------------------------------------
C
       REAL    AXLAM  , KMM     , KT    , KMMINV , MEXMKT , KEXMMT
C
       DATA EPSS/ 1.0E-06 /
C
C================================================================================
C
C                    SETUP
C
C--------------------------------------------------------------------------------
C
       MSE     = 0.0
C
C================================================================================
C
C                    RATE CONSTANT CLOSE TO ARTERIAL RATE CONSTANT
C
C--------------------------------------------------------------------------------
C
       KMM    = RATE    - M
       AXLAM  = ARTENH * LAMBDA
C
       IF ( ABS ( KMM ) .GT. EPSS ) GO TO 300
C
C================================================================================
C
C                    DEGENERATE CASE  ( RATE APPROX EQUAL TO M )
C
C--------------------------------------------------------------------------------
C
          DO 200   NVAL    = 1 , NUMVAL
C
             KT      = RATE    * TMEVAL(NVAL)
             EXPMKT  = EXP ( - KT )                   ; UNDERFLOW SET TO 0.0
             TEMPA   = 1.0 - (1.0 + KT ) * EXPMKT
             TEMPB   = AXLAM   * TEMPA - ENHVAL(NVAL)
C
             MSE     = MSE    + TEMPB * TEMPB
C
 200      CONTINUE
C
          GO TO 600
C
```

```
C=================================================================================
C
C                        NORMAL CASE        ( RATE NOT EQUAL TO M )
C
C---------------------------------------------------------------------------------
C
  300      KMMINV  = 1.0 / KMM
C
           DO 400  NVAL   = 1 , NUMVAL
C
              KT      = RATE      * TMEVAL(NVAL)
              EXPMKT  = EXP ( - KT )                    ; UNDERFLOW SET TO 0.0
C
              MEXMKT  = M * EXPMKT
              KEXMMT  = RATE      * EXPMMT(NVAL)
C
              TEMPA   = 1.0 + ( MEXMKT - KEXMMT ) * KMMINV
              TEMPB   = AXLAM    * TEMPA - ENHVAL(NVAL)
C
              MSE     = MSE      + TEMPB * TEMPB
C
  400      CONTINUE
C
  600      CONTINUE
C
           MSE    = MSE / NUMVAL                         ; NORMALIZE
C
           RETURN
C
           INCLUDE "DIXPRM.IR"
C
           END
```
,494

What is claimed is:

1. A method of determining blood flow in tissue comprising the steps of applying a freely diffusible inert gas to said tissue, obtaining a measure of concentration of said gas in arterial blood as a function of time by breath analysis, obtaining a measure of concentration of said gas in said tissue as a function of time by CT measurements, obtaining the values of the blood flow rate constant (k) and partition coefficient ($\lambda$) by adopting a functional form for the time behavior of gas concentration, and thereafter successively deriving the said volumes of $\lambda$ and K from the partial derivatives of the sum of errors squared of the measured tissue concentration less the measured blood concentration, and determining blood flow in said tissue using said rate constant (k) and partition coefficient ($\lambda$).

2. The method as defined by claim 1 where blood flow is determined from calculated tissue concentration of the freely diffusible inert gas given by $$C(t) = k \int_0^t C_a(u)e^{-k(t-u)}du$$

where, $\lambda$ is the partition coefficient k is the rate constant f=k is flow/volume $c_a(t)$ is the arterial concentration of gas as a function of time.

3. The method as defined by claim 2 wherein the sum of errors squared is given by $$F = \sum_t W_t \left[ \lambda K \int_0^t C_a(u)e^{-k(t-u)}du - C(t) \right]^2 \quad (2)$$

and the partial derivatives are $$O = \frac{\partial F}{\partial \lambda} 2 \sum_t W_t \left\{ \lambda k \int_0^t C_a(u)e^{-k(t-u)}du - C(t) \right\} \quad (3)$$

$$k \int_0^t C_a(u)e^{-k(t-u)}du$$

$$O = \frac{\partial F}{\partial k} = 2 \sum_t W_t \left\{ \lambda k \int_0^t C_a(u)e^{-k(t-u)}du - C(t) \right\}$$

$$\lambda \int_0^t C_a(u)(1 - kt + ku)e^{-k(t-u)}du$$

4. The method as defined by claim 1 wherein said blood flow is cerebral and said freely diffusible inert gas is xenon.

5. A method of determining blood flow in tissue, perfused by an arterial blood supply, comprising the steps of applying a freely diffusible inert gas to said tissue through said arterial blood supply which produces a gas concentration of said freely diffusible inert gas in said tissue given by the Kety-Schmidt equation $$C(t) = k \int_0^t C_a(u)e^{-k(t-u)}du$$

where $\lambda$ is a partition coefficient, k is a rate constant, t is time, u is an integration variable, $C_a(t)$ is the concentration of the freely diffusible inert gas in arterial blood as a function of time, and C(t) is the concentration of the freely diffusible inert gas in tissue as a function of time, obtaining a measure of the concentration of said freely diffusible inert gas in said arterial supply as a function of time, obtaining a measure of the concentration of said freely diffusible inert gas in said tissue at n discrete samples of time given by $t_1$ through $t_n$, obtaining an estimate of said rate constant from the partial derivatives of the sum of squares of the differences of said measured tissue concentration and said Kety-Schmidt equation at each sample time, obtaining an estimate of partition coefficient using said estimate of said rate constant and the partial derivatives of the sum of squares of the differences of said measured tissue concentration and said Kety-Schmidt equation at each sample time, and obtaining said estimate of blood flow by multiplying said estimate of rate constant and said estimate of partition coefficient.

6. The method as defined by claim 5 wherein the sum of the squares of the differences of said measured tissue concentration and said Kety-Schmidt equation is given by $$F = \sum_{i=1}^{n} W_i \left( \lambda k \int_0^{t_i} C_a(u)e^{-k(t_i-u)}du - C(t_i) \right)^2$$

and the partial derivatives are given by, $$\frac{\partial F}{\partial k} = 2 \sum_{i=1}^{n} W_i \left( \lambda k \int_0^{t_i} C_a(u)e^{-k(t_i-u)}du - C(t_i) \right)$$

$$k \int_0^{t_i} C_a(u)e^{-k(t_i-u)}du$$

$$\frac{\partial F}{\partial \lambda} = 12 \sum_{i=1}^{n} W_i \left( \lambda k \int_0^{t} C_a(u)e^{-k(t_i-u)}du - C(t_i) \right)$$

$$\lambda \int_0^{t_i} C_a(u)(1 - kt_i + ku)e^{-k(t_i-u)}du$$

and $W_1$ are weights used to assign different importance to the data values.

7. The method of claim 5 wherein said method of obtaining an estimate of said rate constant includes the step of finding the zero of the function given by $$\frac{\sum_{i=1}^{n} W_i C(t_i) G(t_i,k)}{\sum_{i=1}^{n} W_i E(t_i,k) G(t_i,k)} - \frac{\sum_{i=1}^{n} W_i C(t_i) E(t_i,k)}{\sum_{i=1}^{n} W_i E^2(t_i,k)} = 0$$

where $$E(t_i,k) = k \int_0^{t_i} C_a(u)e^{-k(t_i-u)}du$$

$$G(t_i,k) = \int_0^{t_i} C_a(u)(1 - kt_i + ku)e^{-k(t_i-u)}du.$$

8. The method of claim 7 wherein said method of obtaining an estimate of said partition coefficient from said estimate of said rate constant includes the step of calculating the following equation $$\lambda = \frac{\sum_{i=1}^{n} W_i C(t_i) E(t_i,k)}{\sum_{i=1}^{n} W_i E(t_i,k) G(t_i,k)}$$

9. The method of claim 7 where said method of obtaining an estimate of said partition coefficient from said estimate of said rate constant and includes the step of calculating the following equation $$\lambda = \frac{\sum_{i=1}^{n} W_i C(t_i) E(t_i,k)}{\sum_{i=1}^{n} W_i E^2(t_i,k)}$$

10. The method of claim 5 wherein a mathematical function is used to describe the arterial tissue concentration.

11. The method of claim 10 wherein the mathematical function used to describe the arterial tissue concentration is given by $$C_a(t) = C_{max}(1 - e^{-mt})$$

where $c_{max}$ is a maximum concentration of gas in arterial blood, and m is a rate constant for arterial blood.

12. The method of claim 5 wherein the tissue is cerebral.

13. The method of claim 5 wherein the freely diffusible gas is xenon.

* * * * *

UNITED STATES PATENT AND TRADEMARK OFFICE
CERTIFICATE OF CORRECTION

PATENT NO. : 4,610,258

DATED : September 9, 1986

INVENTOR(S) : James G. Colsher

It is certified that error appears in the above-identified patent and that said Letters Patent is hereby corrected as shown below:

Col. 1, line 15, "Clincal" should be -- Clinical --.

Signed and Sealed this

Twenty-fifth Day of November, 1986

*Attest:*

DONALD J. QUIGG

*Attesting Officer*      *Commissioner of Patents and Trademarks*